(12) United States Patent
Cholette

(10) Patent No.: US 7,751,880 B1
(45) Date of Patent: *Jul. 6, 2010

(54) SHIELDED ELECTRODE ASSEMBLY FOR EFFECTIVE NERVE SENSING AND STIMULATION

(75) Inventor: Martin Cholette, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 373 days.

This patent is subject to a terminal disclaimer.

(21) Appl. No.: 11/673,999

(22) Filed: Feb. 12, 2007

(51) Int. Cl.
*A61N 1/00* (2006.01)

(52) U.S. Cl. .......................................................... 607/2
(58) Field of Classification Search ...................... 607/2
See application file for complete search history.

(56) References Cited

U.S. PATENT DOCUMENTS

| | | | |
|---|---|---|---|
| 4,341,221 A | | 7/1982 | Testerman |
| 4,602,624 A | * | 7/1986 | Naples et al. ............... 607/118 |
| 4,750,499 A | | 6/1988 | Hoffer |
| 4,940,065 A | | 7/1990 | Tanagho et al. |
| 5,031,621 A | | 7/1991 | Grandjean et al. |
| 5,111,815 A | | 5/1992 | Mower |
| 5,215,089 A | | 6/1993 | Baker, Jr. |
| 5,487,756 A | | 1/1996 | Kallesoe et al. |
| 5,623,160 A | * | 4/1997 | Liberkowski ............... 257/621 |
| 5,658,318 A | | 8/1997 | Stroetmann et al. |
| 5,824,027 A | | 10/1998 | Hoffer et al. |
| 5,919,220 A | | 7/1999 | Stieglitz et al. |
| 5,964,702 A | | 10/1999 | Grill, Jr. et al. |
| 6,146,351 A | * | 11/2000 | Kempe ......................... 602/75 |
| 6,292,703 B1 | | 9/2001 | Meier et al. |
| 6,587,725 B1 | | 7/2003 | Durand et al. |
| 6,600,956 B2 | | 7/2003 | Maschino et al. |
| 6,666,821 B2 | | 12/2003 | Keimel |
| 7,006,875 B1 | | 2/2006 | Kuzma et al. |
| 2002/0193697 A1 | | 12/2002 | Cho et al. |
| 2003/0074039 A1 | | 4/2003 | Puskas |
| 2003/0078643 A1 | | 4/2003 | Schulman et al. |
| 2003/0083716 A1 | | 5/2003 | Nicolelis et al. |

(Continued)

FOREIGN PATENT DOCUMENTS

WO 03035165 A1 5/2003

OTHER PUBLICATIONS

Andreasen, Lotte N. S. et al., "Artefact Reduction with Alternative Cuff Configurations," IEEE Transactions on Biomedical Engineering, vol. 50, No. 10 (Oct. 2003).

(Continued)

*Primary Examiner*—George Manuel
*Assistant Examiner*—Shubatra Narayanaswamy

(57) ABSTRACT

A shielded electrode assembly for sensing electrical signals within a nerve is disclosed. The assembly comprises a generally tubular, electrically insulating shield body, which may be reversibly secured to the nerve. An electrically conducting mesh is positioned on at least a portion of an outer surface of the shield body, defining a region of the assembly within which external electromagnetic radiation is significantly attenuated. The conducting mesh is formed by photolithography, providing substantially precise control over the mesh aperture and thus the frequency of radiation which is shielded. A plurality of electrodes are placed within the shielded region and configured so as to contact the nerve. This design allows the electrodes to sense nerve signals within an environment which is at least partially shielded from electromagnetic radiation, facilitating nerve sensing with reduced need for filtering or signal processing.

15 Claims, 8 Drawing Sheets

U.S. PATENT DOCUMENTS

| | | |
|---|---|---|
| 2003/0144710 A1 | 7/2003 | Haugland et al. |
| 2003/0153954 A1 | 8/2003 | Park et al. |
| 2004/0024439 A1 | 2/2004 | Riso |
| 2004/0210261 A1 | 10/2004 | King et al. |
| 2005/0010265 A1 | 1/2005 | Baru Fassio et al. |
| 2008/0023010 A1* | 1/2008 | Inman et al. ............... 128/846 |

OTHER PUBLICATIONS

Office Action, mailed Jul. 19, 2006, Related U.S. Appl. No. 11/045,626.

Final Office Action, mailed Oct. 13, 2006, Related U.S. Appl. No. 11/045,626.

Office Action, mailed Mar. 7, 2007, Related U.S. Appl. No. 11/045,626.

Office Action, mailed Jul. 18, 2007, Related U.S. Appl. No. 11/045,626.

Notice of Non-Complaint Amendment, mailed Oct. 10, 2007, Related U.S. Appl. No. 11/045,626.

Final Office Action, mailed Feb. 25, 2008, Related U.S. Appl. No. 11/045,626.

Advisory Action, mailed May 14, 2008, Related U.S. Appl. No. 11/045,626.

Office Action, mailed Aug. 6, 2008, Related U.S. Appl. No. 11/045,626.

Haugland, Morten., "A Flexible Method for Fabrication of Nerve Cuff Electrodes" IEEE Engineering in Medicine and Biology Society, Amsterdam 1996, 2.2.3: Peripheral Electrodes.

Notice of Allowance, mailed Jan. 29, 2009: Related U.S. Appl. No. 11/045,626.

* cited by examiner

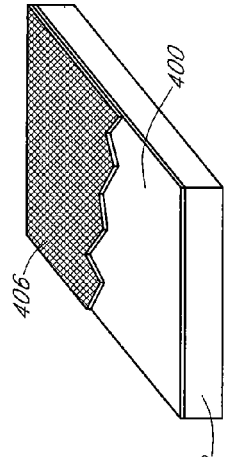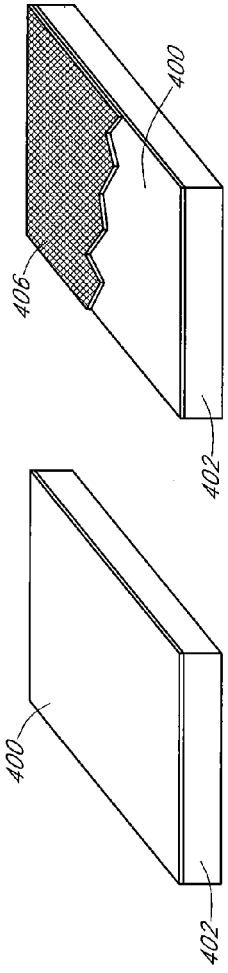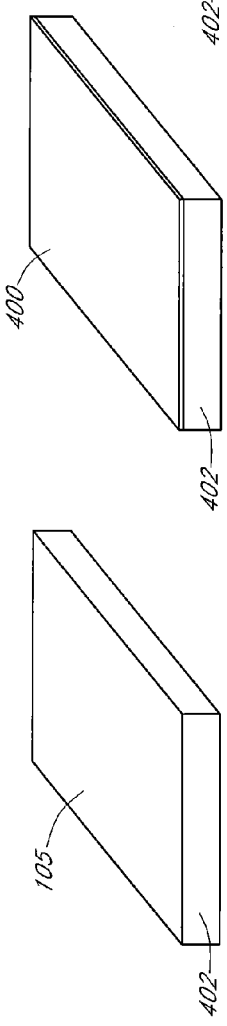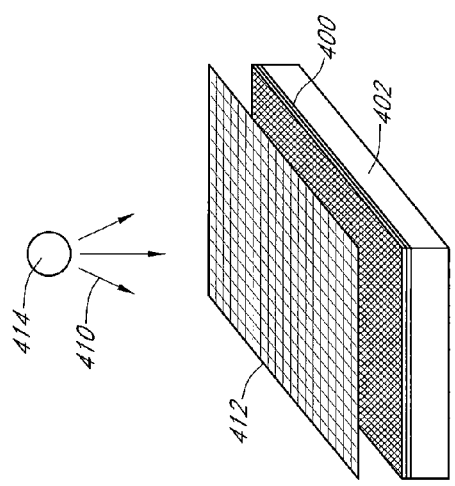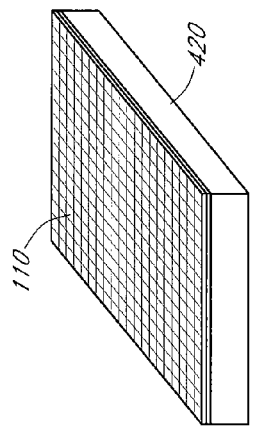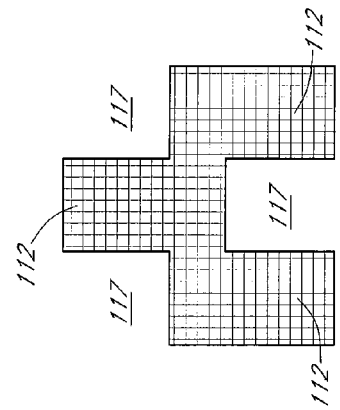

SHIELDED ELECTRODE ASSEMBLY FOR EFFECTIVE NERVE SENSING AND STIMULATION

CROSS-REFERENCE TO RELATED APPLICATIONS

This application is related to copending U.S. patent application Ser. No. 11/045,626, filed Jan. 26, 2005, titled "Shielded Electrode for Nerve Sensing".

FIELD OF THE INVENTION

The invention relates to the field of implantable medical devices and, in particular, to shielded electrodes for in vivo nerve sensing, such as of the vagus or phrenic nerve, and to implantable medical devices employing such sensors.

BACKGROUND OF THE INVENTION

A variety of devices and methods are known for internally sensing physiological activity and providing therapeutic stimulation for a variety of data gathering and therapeutic purposes. For example, implantable stimulation devices are known that automatically, internally sense one or more of the patient's physiological parameters and selectively provide stimulation to nerve tissue as therapy, such as for epileptic conditions, pain treatment, or apnea.

Implantable medical devices which internally sense electrical signals indicative of physiological processes of the patient have typically done so by placing one or more sense electrodes in contact with the associated patient tissue. These electrodes are then connected to appropriate amplifier and/or filter circuits such that the sensed physiologically generated electrical signals are conducted and transformed into a format suitable for analysis and utilization, such as for determination of therapy delivery or clinical data analysis.

Peripheral nerves of the body, such as the vagus or phrenic nerves, offer enticing possibilities for internally measuring the activity of these or other nerves for a variety of possible uses. For example, the phrenic nerve conducts signals originating in the brain to the diaphragm to induce the diaphragm to contract, resulting in an inspiration phase of the patient's cyclic respiration.

The configuration and duration of the nerve activity correlate to the brain's perceived metabolic need for the patient's body. Thus, the ability to directly sense activity on the phrenic nerve would provide information indicative of the inherent perceived respiration demand, rather than inferential information related to respiratory demand, such as systemic $CO_2$ concentration, or to the respiratory response, such as a minute volume measurement. Direct sensing of phrenic nerve activity would also provide the ability to diagnose a central sleep apnea (CSA) condition by directly observing the lack of, or reduced, phrenic nerve activity.

However, such direct nerve sensing, particularly on a chronic or long-term basis, has been inhibited by several factors. A major impediment to direct nerve sensing in the body is accurately discriminating the nerve signals from background electrical signals also present in the patient's body. Nerve activity, such as on the phrenic nerve, is typically of microvolt to fractional microvolt amplitudes and of approximately 300 to 10 kilohertz in frequency. Background "noise", also present within the patient's body adjacent nerves of interest, is typically several orders of magnitude greater, e.g. in the millivolt range, and of comparable frequency spectra. This background noise can arise from the patient's cardiac activity, muscular activity, and conducted electrical signals induced from background electromagnetic energy, such as electrical line supply at 60/50 Hz. Because the background noise can be thousands of times greater in amplitude and covering a comparable frequency range to the signal of interest, e.g. nerve activity, it is a significant technical challenge to isolate the nerve activity of interest from the background noise.

One method of addressing this problem is to physically separate the nerve tissue of interest from other adjacent tissues and to subsequently measure the nerve activity. For example, a portion of nerve may be surgically exposed and moved away from adjacent body tissues. This action physically isolates the distanced portion of the nerve, attenuating the portion of the signal carried in the nerve associated with background noise compared the nerve activity of interest. Sensing electrodes may then be attached to the nerve to sense signals directly from the nerve. The signals sensed may be processed through appropriate amplifier and filter circuits in order to further isolate the physiological signal from the background noise.

This procedure is not desirable for long-term monitoring, however. For example, there is no guarantee that the nerve will remain isolated over time. Physical activity, injury, or aging may result in movement of the nerve from a surgically designated position back to its original position, or another non-optimal position, degrading the quality of the signal measured in the nerve.

Furthermore, while methods and procedures are known which might be adapted for at least somewhat effectively isolating a nerve signal from background noise, they are typically highly demanding of processor speed and power. For example, a sensed signal can be digitized and processed with a variety of digital signal processing (DSP) algorithms. However, such DSP algorithms typically are far too demanding of processor capability and power consumption than is permissible within the available processing bandwidth and limited battery capacity of an implantable device. Digital filtering offers limited assistance as the frequency spectra of nerve signals is comparable to that of the background noise.

Thus it will be appreciated that there is a need for accurate, reliable direct sensing of nerve activity which is suitable for long-term chronic use, such as by a battery powered implantable medical device. There is also a need for a device which can accurately sense low level signals in an environment with relatively high amplitude noise of comparable frequency spectra and provide these signals in a manner for effective use which does not overburden the available processing bandwidth or power consumption available to a battery powered implantable medical device. It would be further advantageous to provide a sensing system which facilitates implantation by the clinician and the flexibility for application to multiple nerves.

SUMMARY

An embodiment of the present disclosure provides a sensor for sensing the electrical activity within a nerve. The sensor comprises a sensor body having first and second surfaces adapted to be positioned proximate to the nerve so as to be able to sense electrical activity within the nerve. The sensor further comprises at least one electrode formed adjacent the first surface of the sensor body so as to be able to either sense electrical activity within the nerve or deliver electrical stimulation to the nerve when the sensor body is positioned proximate to the nerve. The sensor additionally comprises a shielding element coupled to the sensor body, where the shielding element is insulated from the at least one electrode. Additionally, the shielding element possesses a plurality of openings and is adapted to shield the at least one electrode from electromagnetic radiation to improve the ability of the at least one electrode to sense electrical activity within the nerve.

Another embodiment of the present disclosure provides a system for providing therapeutic stimulation to the heart of a patient. The system comprises at least one lead having at least one electrode adapted to be implanted within the heart of the patient so as to sense electrical activity within the heart of the patient and to deliver electrical therapeutic stimulation to the heart of the patient. The system further comprises a nerve electrode assembly adapted to be positioned proximate a nerve so as to sense electrical activity within the nerve. The nerve electrode assembly includes a body that is adapted to be fixed proximate the nerve, at least one nerve electrode that senses electrical signals within the nerve, and is formed proximate a first surface of the body and a shield possessing a plurality of openings that is formed proximate a second surface of the body in a location. The shield inhibits electromagnetic radiation from sources other than the nerve to be sensed by the at least one nerve electrode. The system additionally comprises a controller that receives signals from the at least one lead and the nerve electrode and uses the signals to develop therapeutic electrical stimulation to the heart of the patient via the at least one lead.

A further embodiment of the present disclosure provides method of forming a sensor for sensing electrical activity within a nerve. The method comprises forming a sensor body having a first and a second surface adapted to be positioned proximate the nerve so as to be able to sense electrical activity within the nerve. The method also comprises forming at least one electrode adjacent the first surface of the sensor body so as to be able to either sense electrical activity within the nerve or deliver electrical stimulation to the nerve when the sensor body is positioned proximate to the nerve. The method additionally comprises forming a shielding element coupled to the sensor body. The shielding element is insulated from the at least one electrode and possesses a plurality of openings. The shielding electrode is also adapted to shield the at least one electrode from electromagnetic radiation to thereby improve the ability of the at least one electrode to sense electrical activity within the nerve.

BRIEF DESCRIPTION OF THE DRAWINGS

FIGS. 4A-4E illustrate one embodiment of a lithographic deposition process for placement of the conducting elements of the electrode assembly of FIG. 1;

FIG. 4F illustrates one embodiment of a final shape of the shield body of the electrode assembly of FIG. 1;

DETAILED DESCRIPTION OF THE PREFERRED EMBODIMENT

Figure 1A:
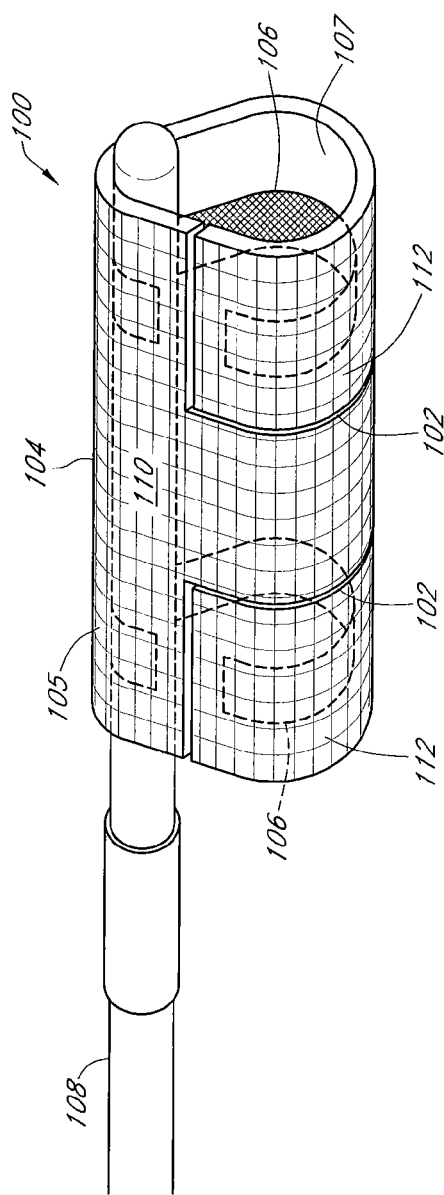
FIGS. 1A-C illustrate perspective and cross-sectional views of one embodiment of a shielded electrode assembly of the present disclosure; (A) engaged position; (B) side view; (C) disengaged position.
Figure 1B:
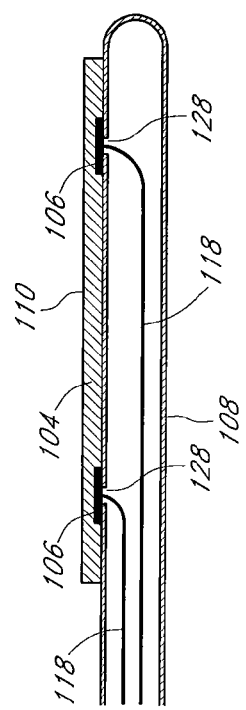

Embodiments of the present disclosure provide an electrode assembly 100 possessing an enveloping conductive element 110 which acts to provide shielding from electrical noise. The shielded electrode assembly 100, illustrated in FIGS. 1A-B, is configured to be readily positioned proximate to a nerve 200 (FIG. 2) in order to sense nerve activity on the nerve 200 while providing improved isolation from external electrical noise which may be present within the patient's body. As will be described herein below, in one preferred embodiment, photolithographic techniques are employed to provide the conductive element, such as a mesh, on at least a portion of an outer surface 105 of the electrode assembly 100 for shielding purposes.

In one implementation, the electrode assembly 100 may be designed for long-term implantation and use with implantable medical devices capable of providing therapeutic stimulation. In another implementation, the conductive element 110 greatly enhances the nerve sensing ability of the shielded electrode assembly 100 without substantially impacting its ability to stimulate the nerve 200. In another advantage, the conductive element 110 may be readily implemented in a cost-effective manner through photolithography. Thus, the shielded electrode assembly 100 provides efficient stimulation and sensing at substantially the same time, a combination which has previously been difficult to achieve. These and other objects and advantages of the present disclosure are discussed in detail below.

Figure 1C:
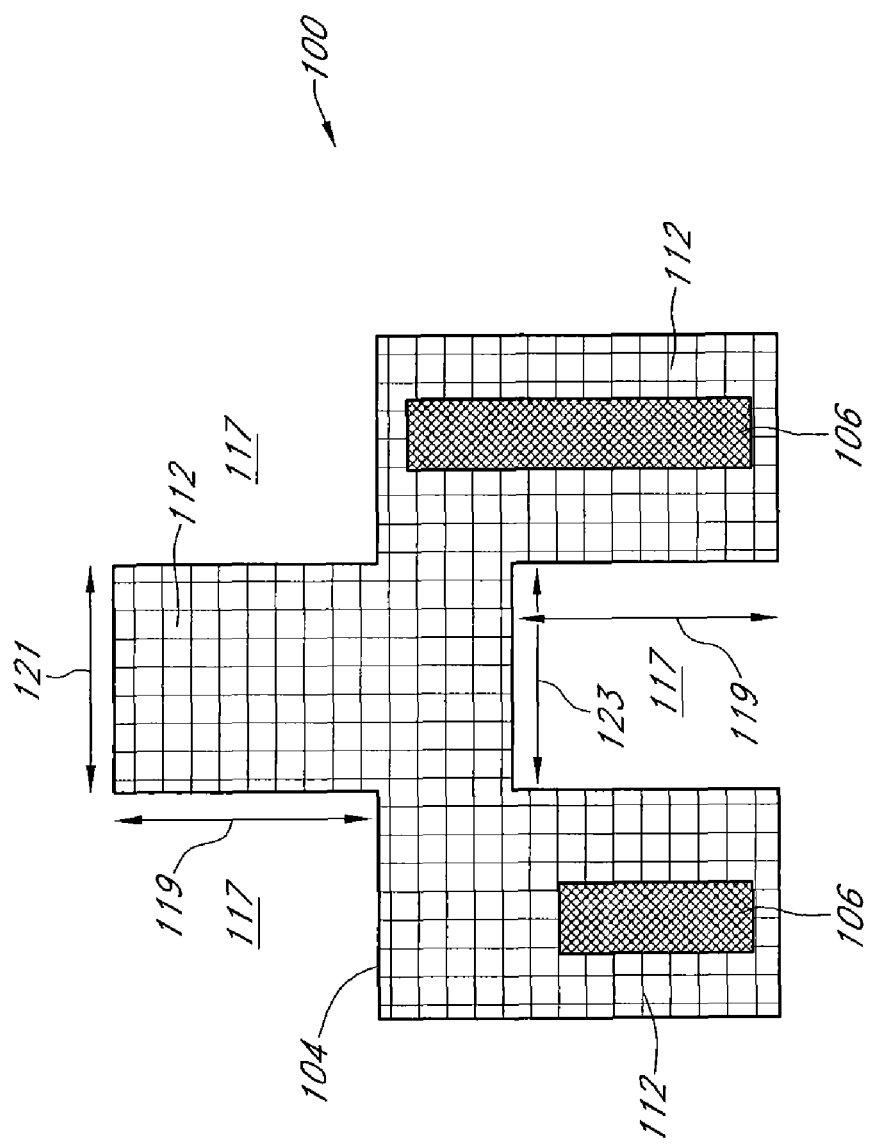

FIGS. 1A-C illustrate perspective and cross-sectional views of one embodiment of a shielded electrode assembly 100. In one embodiment, the shielded electrode assembly 100 comprises a shield body 104, electrodes 106, an insulating lead body 108, and the conducting element 110.

The shield body 104 defines a generally tubular body of the shielded electrode assembly 100 having an outer surface 105 and an inner surface 107. As illustrated in the embodiment of FIGS. 1A and 1C, the shield body 104 contains slits 102 which form generally rectangular fingers 112 that extend outward from an elongate center portion 114 of the shield body 104. The fingers 112 are configured to be placed in corresponding spaces 117 opposite the fingers 112. In one embodiment, the length 119 of the spaces 117 and fingers 112 are approximately equal, while the width 121 of the spaces 117 is approximately less than the width 123 of the fingers 112.

This configuration allows the shield body 104 to move between an engaged position (FIG. 1A) and a disengaged position (FIG. 1C). In the disengaged position, the fingers 112 of the shield body 104 are substantially separated from one another, allowing the shield body 104 to be positioned proximate to an object, e.g. about, such as a nerve 200. In the engaged position, the shield body 104 is curled upon itself into a tubular shape proximate to the nerve 200. In so doing, the fingers 112 are positioned within corresponding spaces 117, across the center portion 114 from the fingers 112. As the width 121 of the spaces 117 are dimensioned to be approximately less than that of the fingers 112, the fingers 112 experience a compressive force along at least a portion of their length 119 due to the constraint of the adjacent fingers 112. This compressive force gives rise to frictional resistance when the fingers 112 are subsequently disengaged to move the shield body 104 from the engaged to disengaged positions. As a result, the fingers 112 may be substantially locked in place once positioned by a medical professional during implantation of the electrode assembly 100, allowing the shield body 104 to maintain its shape during use. In one implementation, the electrode assembly 100 can resiliently bear upon the outer surface of the nerve 200 so as to establish and maintain good electrical contact with the nerve 200. Alternately the body 104 may be sized so as to be spaced away slightly from the nerve to reduce the risk of damage to the nerve.

In one embodiment, the shield body 104 comprises a biologically compatible polymer material. Examples may include, but are not limited to, silicones, polyurethanes, and co-polymers thereof. As discussed below with respect to the method of fabricating the electrode assembly 100, in one embodiment, the shield body 104 may comprise a single layer of the polymer material or two layers of the polymer material with a conducting metal layer interposed between.

In one embodiment, the shield body 104 may be biased towards the engaged position. For example, the polymer shield body 104 may be molded in a generally tubular shape such that the fingers 112 are positioned substantially in, or near, the engaged position at rest. As a result, when moving from the engaged to disengaged position, the shield body 104 is deformed elastically in order to position the nerve 200 proximate to the electrode assembly 100. Advantageously, this biased design maintains the generally tubular shape of the shield body 104, even when the fingers 112 are disengaged from one another, inhibiting complete disengagement of the electrode assembly 100 from the nerve 200 once positioned proximate the nerve 200, even in the event that the fingers are disengaged.

The strength with which the fingers 112 interlock in the engaged position may be adjusted by varying the number of fingers 112 present in the shield body 104, as well as their length 119 and their width 121 compared to the width 123 of their corresponding spaces 117. This change in interlocking strength is due to the variation in the amount of contact area between the fingers 112 and the compressive force applied to the fingers 112 by adjacent fingers 112 when positioned within the spaces 117. For example, increasing the number of fingers 112 and the length 119 of the fingers 112 and spaces 117 increases the contact area between adjacent fingers 112. Furthermore, decreasing the width 123 of the spaces 117 with respect to the width 121 of the fingers 112 (or conversely increasing the width 121 of the fingers 112 with respect to the width 123 of the spaces 117) increases the compressive stress experienced along the contact area between adjacent fingers 112. These two effects together cause the frictional resistance to disengagement of the fingers 112 to increase, increasing the applied stress required disengage the fingers, and thus the interlocking strength.

In one embodiment, as illustrated in FIGS. 1A and 1C, three fingers 112 of equal length may be formed in the shield body 104. However, it may be understood that the shield body 104 may be configured with greater or fewer fingers 112, as necessary. For example, the shield body 104 may be provided with four fingers 112 if greater interlocking strength is required compared to a three finger 112 shield body 104 of otherwise substantially equivalent geometry, while the shield body 104 may be provided with two fingers if less interlocking strength is required compared to a three finger 112 shield body 104 of otherwise substantially equivalent geometry. Alternatively, the length 119 of the fingers 112 may be increased, while keeping the width 123 of the spaces 117 and the number of fingers 112 constant, in order to increase the strength of interlocking. Further, the length of the fingers 112, the width of the fingers 112, the width of the spaces 117, and the number of fingers 112 may be adjusted simultaneously, as necessary, in order to tailor the interlocking strength of the shield body 104, as discussed below.

Figure 2:
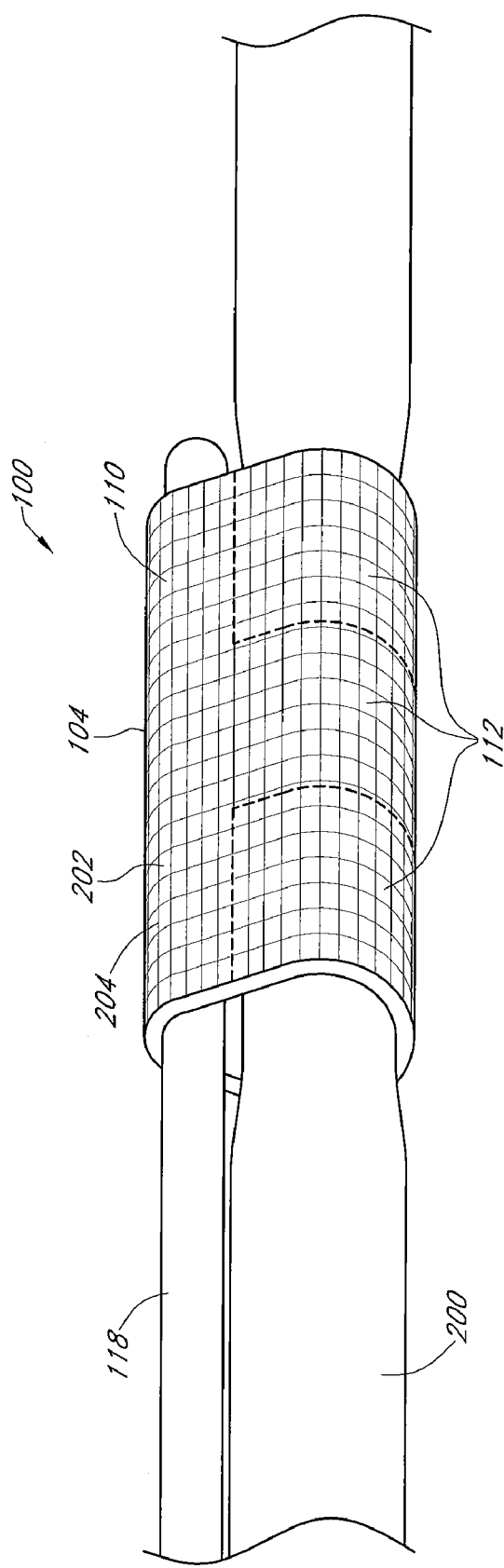
FIG. 2 illustrates a perspective view of the shielded electrode assembly of FIG. 1 positioned proximate to a nerve.

Advantageously, the interlocking finger design of the shield body 104 allows the diameter of the shield body 104 to be adjusted. As illustrated in FIG. 2, when deployed, the shield body 104 extends around the circumference of the nerve 200, with the fingers 112 in the engaged position in order to secure the shield body 104 in place. Depending on the size of the nerve 200, the portion of the total length 119 over which the fingers 112 interlock may be adjusted in order to change the diameter of the shield body 104. Thus, in one aspect, the diameter of the shield body 104 may be varied by the medical professional when the electrode assembly 100 is implanted, allowing the electrode assembly 100 to accommodate nerves 200 of varying size. This ability to adjust the diameter of the shield body 104 provides an electrode assembly 100 capable of being implanted about a range of sizes of nerves, thereby reducing the need for electrode assemblies 100 of multiple sizes, reducing the cost of providing nerve stimulation.

The interlocking finger design of the shield body 104 also enhances the ease of implantation and long term durability of the electrode assembly 100. Conventionally, suturing may be utilized in order to position electrode assemblies proximate to a nerve 200. However, sutures may stretch, break, or come undone over time, releasing the electrode assembly from its desired position.

The shield body 104 of the present disclosure interlocks with itself, however, functioning as its own fixation mechanism. As a result, additional fixation mechanisms which lock the shield body 104 in place are less necessary. For example, the geometry of the fingers 112 and spaces 117 may be adjusted so that the fingers 112 interlock with strength sufficient to withstand stresses experienced during use, and maintain the position of the electrode assembly 100. Thus, to secure the electrode assembly 100 proximate to the nerve 200, the electrode assembly 100 is simply positioned circumferentially about the nerve 200, the fingers 112 are placed within the spaces 117, and the length over which the fingers 112 interlock is adjusted according to the diameter of the nerve 200.

The shield body 104 may further be used in conjunction with other fixation mechanisms. Advantageously, the interlocking finger design of the shield body 104 does not interfere with the efficacy of fixation mechanisms such as suturing. Thus, the shield body 104 may allow the use of multiple fixation mechanisms, enhancing the likelihood that the electrode assembly 100 will remain in its designated position during long-term use.

The diameter of the shield body 104 may also be varied so as to control the amount of pressure applied to the nerve 200 by the shield body 104. In one aspect, exerting modest pressure on the nerve 200 may be important for maintaining the position of the electrode assembly 100 with respect to the nerve 200. Further, this pressure allows the electrodes 106 to maintain good electrical contact with the nerve 200. Good electrical contact in turn provides more efficient nerve stimulation, as it reduces the total amount of energy expended in order to deliver a selected amount of energy to the nerve 200.

The adjustable capability of the shield body 104 further allows the assembly 100 to adapt to changing conditions within the patient's body after implantation. Often, after implantation of the electrode assembly 100, the nerve 200 may swell temporarily, increasing in diameter. When using a fixed diameter shield body, the swollen nerve may be constrained by the shield body, and the pressure exerted by the shield body on the nerve increases with the swelling. Unaddressed, this pressure may rise above a critical value of pressure beyond which impairment or death of the nerve may occur.

Use of the assembly 100 may reduce this problem, however. As described above, the shield body 104 may be configured with a selected interlocking strength at which the fingers 112 begin to disengage. In this context, the interlocking strength may be selected with respect to the critical pressure. For example, the interlocking strength may be selected such that the fingers 112 of the shield body 104 begin to disengage when the nerve 200 experiences a pressure which is less than the critical pressure. Thus, the shield body 104 of the electrode assembly 100 is capable of self-adjusting its diameter while implanted within the patient, reducing the likelihood of damage in the event of swelling of the nerve 200.

In further reference to FIGS. 1A-1C, the electrodes 106 are positioned on the inner surface 107 of the shield body 104, separated by a selected distance. For example, the electrodes 106 may be placed at opposite ends of the shield body 104. The electrodes 106 further span at least a portion of the length 119 of the fingers 112 of the shield body 104. Thus, as the length of the electrodes 106 increases, the fraction of the total circumference of the nerve 200 spanned by the electrodes 106 increases. This positioning allows the electrodes 106 to circumferentially contact the outer surface of the nerve 200 when the shielded electrode assembly 100 is deployed so as to achieve good electrical contact therewith.

Leads 118 are connected to the electrodes 106, through openings 128 in the shield body 104. The leads 118 extend away from the electrodes 106, conducting sensed activity of the nerve for further analysis. The leads 118 may also be used to conduct stimulation signals to the electrodes 106. In one embodiment, the leads 118 are housed in the insulating lead body 108 for protection.

A plurality of electrodes 106 and leads 118 may be provided within a single shielded electrode assembly 100. In one embodiment, multiple sensing pairs, triplets, etc. may be provided. In an alternative embodiment, multiple electrodes 106 can be electrically coupled. For example, a single pair of electrodes 106 may be positioned on opposite ends of the shield body 104, as illustrated in FIGS. 1A-C. In another example, two pairs of electrodes 106 may be used, with alternating electrodes 106 electrically coupled with each other. Advantageously, multiple pairs of electrically coupled electrodes 106 allow evaluation of relative timing/potential differences of signals sensed between the coupled electrode pairs to determine the direction of propagation of signals along the nerve 200.

In one embodiment, at least a portion of the electrodes 106 are substantially surrounded by the conducting element 110, and therefore positioned within the shielded region provided by the conducting element 110. Thus, relatively high magnitude electrical noise, such as that arising from cardiac activity, muscular activity, or conducted or radiated electromagnetic energy, is more effectively isolated from the shielded portion of the nerve 200. This shielding allows the shielded electrode assembly 100 to more easily sense relatively small magnitude electrical signals of interest, such as activity on the nerve 200, which may be several orders of magnitude lower in amplitude than the background noise and of comparable frequencies. A relatively clean signal can therefore be sensed from the nerve 200, thus reducing or eliminating the need for filtering or signal processing to evaluate the sensed activity of the nerve 200. Advantageously, the element 110 performs this shielding function without the need for electrical power, contributing to the energy efficiency of the assembly 100.

As can be further be seen in FIGS. 1A-1B, the shield body 104 is interposed between the conducting element 110 and electrodes 106. As the shield body 104 comprises an electrically insulating polymer material, the shield body 104 serves to insulate the electrodes 106 from the conductive element 110 so as to substantially electrically isolate the electrodes 106 from the conductive element 110, as well as isolate the element 110 from the surface of the nerve 200, further facilitating sensing within the shielded region defined by the conductive element 110.

In one embodiment, the conducting element 110 comprises a mesh 110 defined by a plurality of interconnected metal lines 204 having openings 202 formed between the lines 204 (FIG. 2). The lines 204 may be configured in any suitable geometry for shielding. For example, the metal lines 204 may be oriented at substantially right angles to one another. In other examples, the lines 204 may curve and/or intersect at substantially non-right angles. It may be understood, however, that the conducting element 110 may be substantially solid without departing from the scope of the invention.

The degree of electromagnetic shielding provided by the conductive element 110 is dictated, at least in part, by the dimensions of the openings 202 compared to the wavelength of the radiation. In general, electromagnetic radiation does not penetrate significantly through the mesh 110 when the largest dimension of the openings 202 is less than about a wavelength of the radiation. When the largest dimension of the openings is substantially greater than a wavelength of the radiation, however, the radiation extends further within the mesh 110. Thus, the size of the openings 202 dictates a "cutoff" wavelength above which at least a portion of electromagnetic radiation external to the mesh 110 is substantially attenuated and therefore inhibited from interfering with nerve sensing. Below this cutoff wavelength, electromagnetic radiation is less effectively attenuated and may substantially interfere with nerve sensing. The cutoff may alternatively be described in terms of the frequency that corresponds to the wavelength. In a preferred embodiment, the openings 202 are dimensioned such that their largest dimension is very much less than the wavelength of the electromagnetic radiation which the mesh 110 is intended to shield. For example, the largest dimension of the openings 202 may be selected to be more than 5 times less than the wavelength. In another embodiment, the openings 202 may be configured to attenuate electromagnetic radiation having a frequency less than about 10 kHz.

The mesh geometry may also provide advantages over a solid conductor. In one aspect, the mesh may utilize substantially less conductive material than the solid conductor, thus reducing the cost of manufacture of the electrode assembly 100. In another aspect, the conducting mesh 110 is substantially more flexible than a solid conductor. As a result, the mesh conductor 110 is less likely to bias the shield body in any particular orientation, compared to the solid conductor. Furthermore, the mesh conductor 100 is also less prone to delamination during movement of the nerve, compared to the solid conductor.

FIGS. 3A-D and 4A-F illustrate embodiments of a method of forming the electrode assembly. It may be understood, however, that the order in which the steps of the method, discussed below, are performed may be rearranged without departing from the spirit of the invention.

Figure 3A:
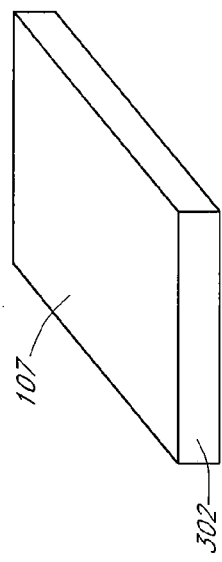
FIGS. 3A-3D illustrate embodiments of a method of manufacturing the electrodes of the electrode assembly of FIG. 1; (A-B) single layer shield body; (C-D) sandwich structure shield body.

In the first step of the method, FIG. 3A, a first polymer layer 302 which forms the shield body is obtained. As discussed above, the polymer comprises bio-compatible polymers which may include, but are not limited to, silicones, polyurethanes, and co-polymers thereof. In one embodiment, the polymer may be commercially obtained. In an alternative embodiment, the polymer may be cast from a liquid polymer formulation, as known in the art.

Figure 3B:
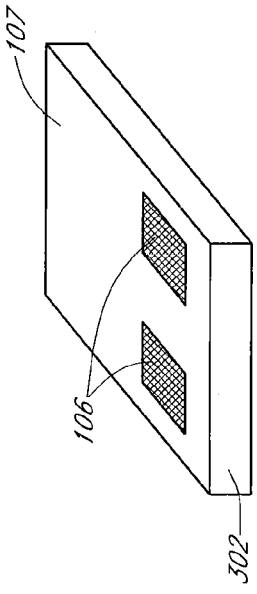

In the second step of the method, the electrodes 106 are formed. In one embodiment, at least a portion of the surface of the first polymer layer 302 designated for use as the interior surface 107 of the shield body 104 is covered with metal for the electrode 106 (FIG. 3B). For example, metallic foils may be affixed to the shield body for this purpose. Alternatively, metal deposition techniques as known in the art, such as vapor deposition, may be utilized to deposit the metal for use as the electrode 106. Preferably, the electrodes 106 comprise a platinum-iridium alloy, however other biocompatible metals, such as gold, may be utilized as well.

Figure 3C:
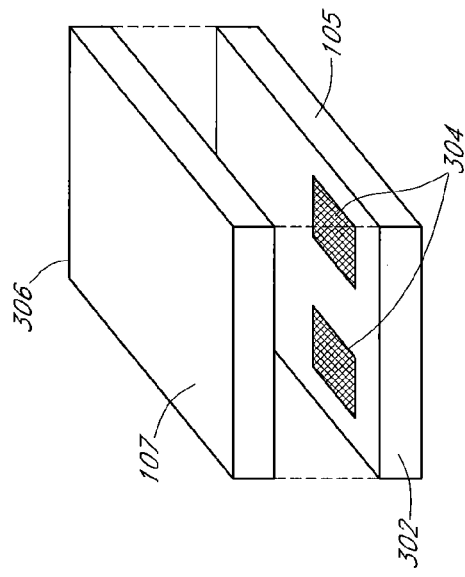
Figure 3D:
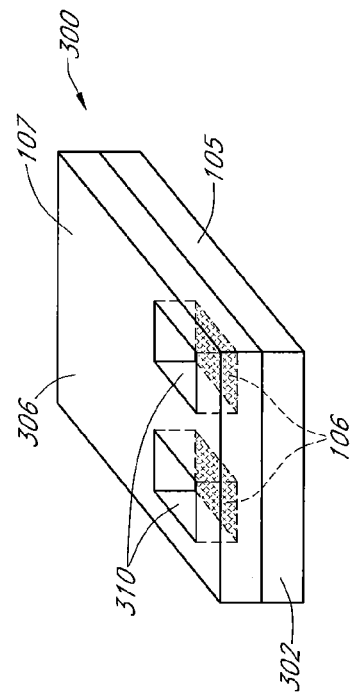

In an alternative embodiment, the electrodes are incorporated within a sandwich structure 300 (FIG. 3D) of the shield body. As illustrated in FIG. 3C, first and second polymer layers 302 and 306 are obtained. For example purposes, it will be assumed that the first layer 302 forms the outer surface 105 of the shield body and the second polymer layer 306 forms the inner surface 107 of the shield body. It may be understood, however, that the layers may be reversed without departing from the spirit of the invention. In this embodiment, metal 304 may be placed on either of the inward facing surfaces of the polymer layers 302, 306. Subsequently, a through-thickness portion of the second polymer layer 306, adjacent to the metal 304, is removed so as to create a window 310 which exposes the underlying metal 304 for use as an electrode 106. The window 310 formed by machining techniques as known in the art, which may include, but are not limited to, manual cutting, milling and laser cutting.

Advantageously, exposing the metal 304 for the electrodes 106 provides significant flexibility in the configuration of the electrodes 106. For example, a plurality of large, non-contiguous metal layers 304 may be sandwiched between the two polymer layers 302, 306. So configured, the position, size, and shape of the window determine the position, size, and shape of the electrodes 106. As a result, the configuration of the electrodes 106 is not determined until the windows 310 are formed.

In one embodiment, the conducting element 110, such as a mesh 110, is deposited on the shield body 104 after formation of the electrodes 106. Advantageously, forming the conducting element 110 directly on the shield body 104 provides a conducting element 110 which is substantially resistant to delamination. Thus, forming the conducting element 110 in this fashion provides a mechanically robust electrode assembly 100.

In an alternative embodiment, the conducting element 110 is formed on a thin, flexible substrate. The substrate may subsequently be affixed to the shield body 104. An adhesive or other biocompatible fixation mechanism may be used for this purpose. This configuration has the advantage that the conducting element 110 may be quickly and easily applied to the shield body 104. As a result, electrode assemblies may be formed without shielding and later converted into shielded electrode assemblies 100 in very little time, without dedicated fabrication.

In the following discussion, it is assumed that the conducting element 110 is positioned on the outer surface 105 of the shield body 104. However, in alternative embodiments, the conducting element 110 may be embedded within the shield body 104 without departing from the spirit of the invention. For example, the conducting element 110 may be positioned within a multi-layer sandwich structure, as described above. Alternatively, the shield body 104 may be molded about the conducting element 110.

In one embodiment, photolithography may be utilized to form the conducting element 110 (FIGS. 4A-F). Generally, photolithography is a technique which allows patterning of a layer of conductive metal. The process begins with a thin, flexible substrate or polymer layer 402. In one embodiment, the polymer layer 402 may comprise the first polymer layer 302 or sandwich structure 300 discussed above.

A layer of conductive metal 400, typically several nanometers thick, is deposited on the surface of the polymer or substrate 402 intended for use as the outer surface 105 of the shield body 104 (FIG. 4B). Preferably the metal 400 comprises a platinum-iridium alloy, however other biocompatible metals, such as gold, may be utilized as well. A layer of photoresist 406, a chemical formulation that chemically reacts when exposed to light 410, is then applied upon the metal layer (FIG. 4C). Typically the light 410 comprises ultraviolet light. Subsequently, a transparent plate with opaque areas printed on it, referred to as a photomask 412, is placed between a light source 414 and the polymer or substrate 402 (FIG. 4D). Activation of the light source 414 causes the photoresist exposed to the light 410 to undergo a chemical reaction. Subsequently, the photoresist 406 is heat treated in order to stabilize the photoresist 406 prior to subsequent processing. After the heat treatment, the metal-photoresist 406 is exposed to chemical solutions which remove selected portions of the metal and photoresist, forming a blank 420 upon which the desired geometry of the conducting element 110 is formed (FIG. 4E).

The photoresist 406 may comprise either "positive" and "negative" forms. With positive resists, as described above, the area that is opaque (masked) on the photomask 412 corresponds to the area where photoresist 406 will remain upon chemical exposure and hence where metal 400 will remain at the end of the photolithography. Alternatively, with negative resists, the area that is not masked on the photomask 412 will remain upon chemical exposure, defining the region where metal 400 will remain at the end of the photolithography process.

In one embodiment, the conducting element 110 is formed in a mesh-like geometry. A person of ordinary skill in the art will appreciate that any of a number of different types of materials can be used to form the mesh. For example, platinum, stainless steel, iridium and titanium are examples of conducting material that are generally biocompatible and would provide a conducting grid for shielding purposes. A person of ordinary skill in the art will also appreciate that the size of the grid openings will vary depending upon the implementation but, as an example, openings that are 1 mm square or less would be suitable for some implementations.

In one embodiment, the blank 420 may subsequently be stored for future use. In another embodiment, the blank 420 may be formed into selected geometries and then stored for further use (FIG. 4F). For example, fingers 112 and spaces 117 may be formed to provide an interlocking shield body, as discussed above. Such forming may comprise machining operations which may include, but are not limited to, manual cutting, milling and laser cutting.

It may be understood that the order of processing operations may be rearranged, as necessary. For example, the mesh 110 may be placed on the polymer 402 prior to formation of the electrodes. In another example, the polymer 402 may be machined to shape prior to placement of either the electrode 106 or the mesh 110.

Photolithographic processing is advantageous for a number of reasons. In one aspect, photolithography may afford substantially exact control, down to the micron and even sub-micron level, over the shape and size of the conducting mesh formed on the polymer or substrate 402. Thus, the technique allows substantially precise control over the wavelengths of electromagnetic radiation which is shielded by the electrode assembly. In another aspect, photolithography can create patterns over a large area in a single process. Thus, the conducting element may be formed over the entire surface of the shield body through a single lithographic process. In a further aspect, the patterns formed through photolithography are substantially identical from one run to the next, providing excellent quality control. In another advantage, photolithographic techniques may be adapted for batch fabrication, allowing mass production and economies of scale which may reduce the manufacturing cost of the electrode assembly.

Thus, the shielded electrode assembly 100 is suitable for long-term implantation within a patient and for providing direct nerve sensing which is substantially shielded from external noise, particularly noise of greater amplitude and of similar frequency spectra. This facilitates direct nerve sensing while reducing the need for filtering or signal processing which is highly demanding of processing and power supply capabilities. Thus, as described in greater detail below, the shielded electrode assembly 100 readily enables implantable medical devices, such as implantable cardiac stimulation devices, to directly monitor nerve activity for better evaluation of the patient's condition as well as to more effectively enable the devices to deliver therapy when indicated, such as to mitigate episodes of central sleep apnea (CSA) or to more accurately track therapeutic pacing to the patient's metabolic demand.

Figure 5:
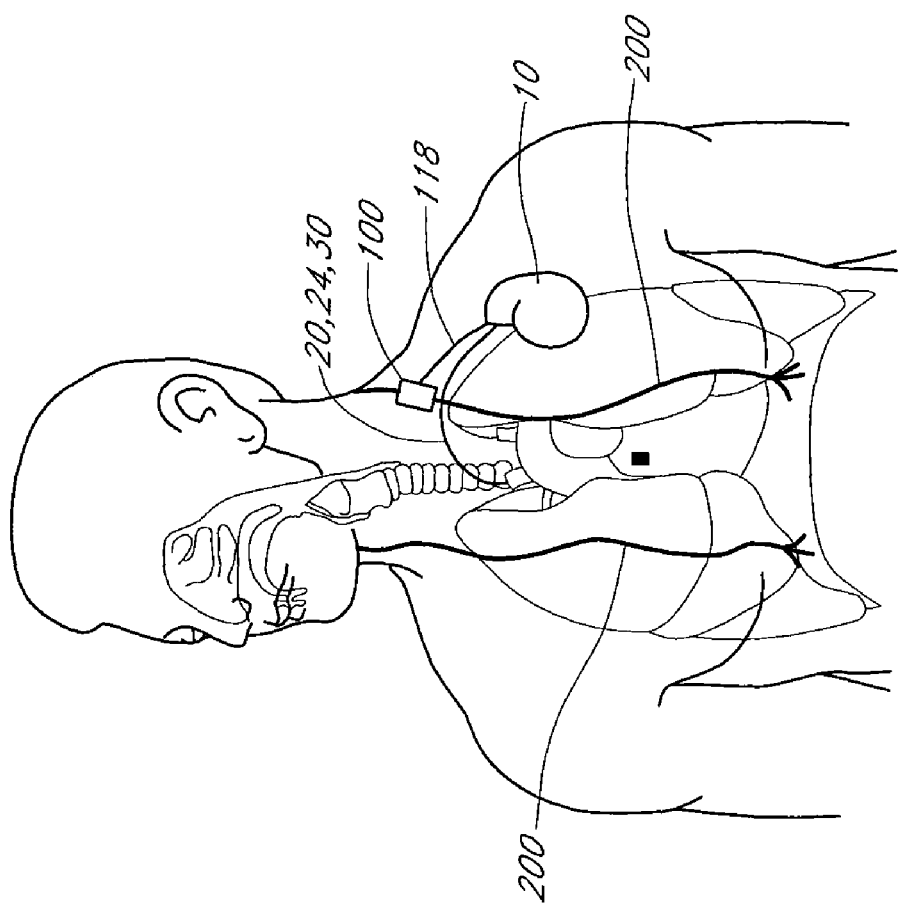
FIG. 5 illustrates embodiments of the shielded electrode positioned proximate to an implantee's phrenic nerve and in communication with an implantable medical device.

FIG. 5 illustrates one embodiment of use of a shielded electrode assembly 100 in concert with an implantable cardiac stimulation device 10 to sense a nerve 200. In this embodiment, the shielded electrode assembly 100 is applied to the patient's phrenic nerve 200 to sense phrenic nerve activity. Thus, signals sensed on the phrenic nerve 200 can be conducted by the leads 118 of the electrode assembly 100 to the implantable cardiac stimulation device 10 to provide information to the device 10 relating to directly sensed activity on the phrenic nerve 200.

Figure 6:
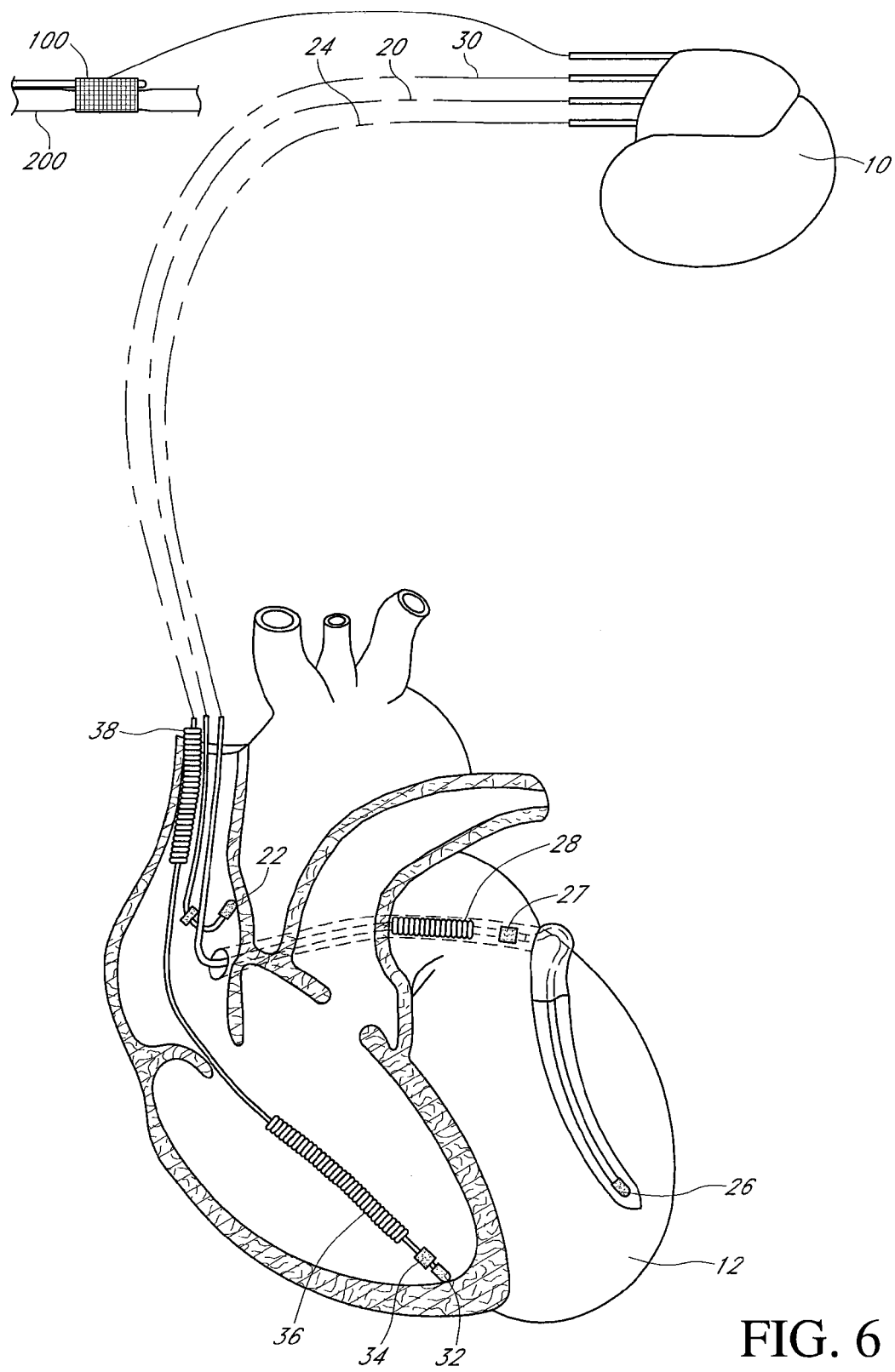
FIG. 6 is a simplified diagram illustrating an implantable stimulation device in electrical communication with at least three leads implanted into a patient's heart for delivering multi-chamber stimulation and shock therapy as well with a nerve.

As shown in greater detail in FIG. 6, one or more shielded electrode assemblies 100 is applied to corresponding nerve(s) 200, such as the phrenic and/or vagus nerves, and is further connected to the device 10. The implantable stimulation device 10, referred to hereafter as "device 10" for brevity, is also in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium (OS) for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an superior vena cava (SVC) coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

Figure 7:
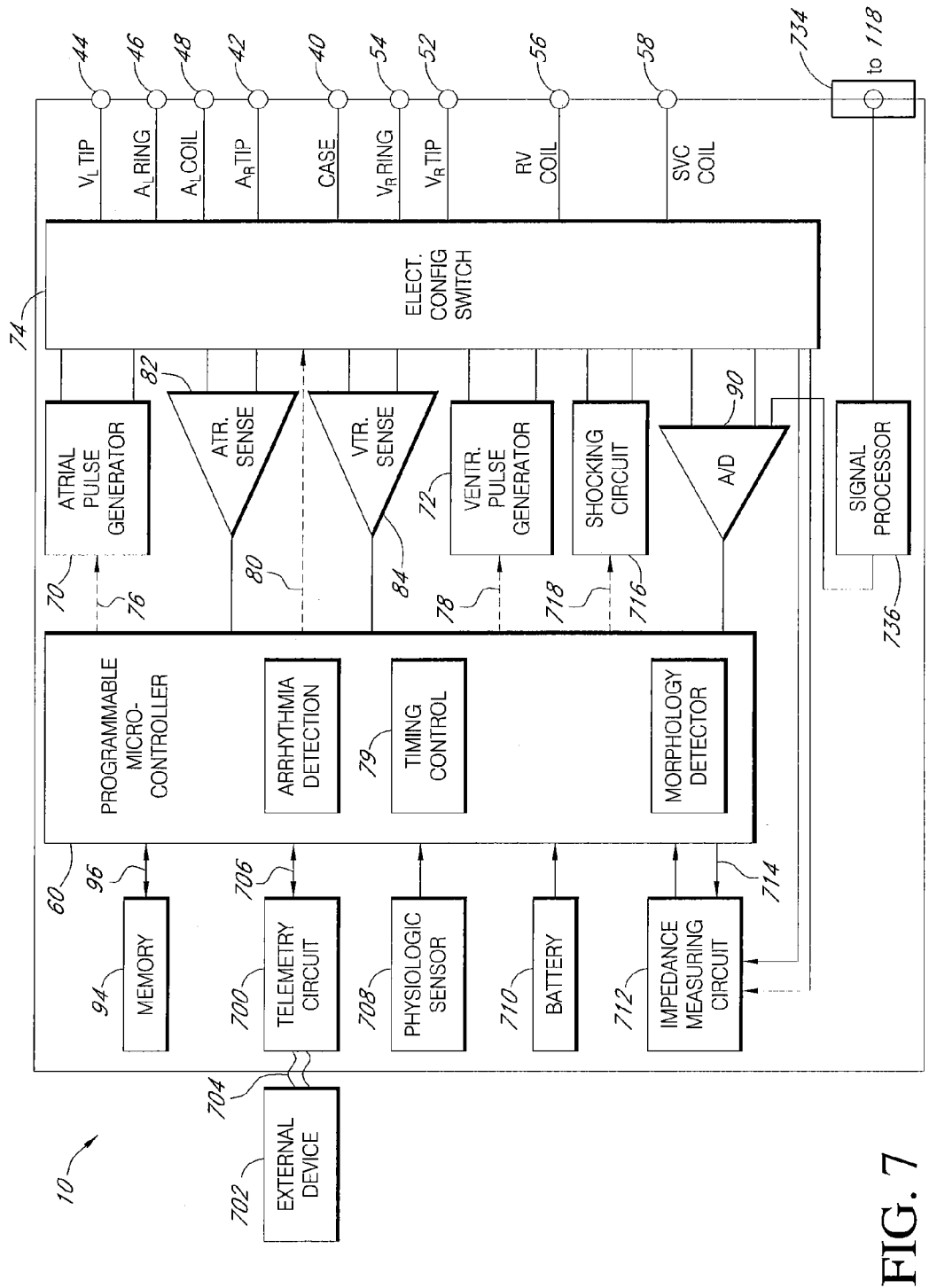
FIG. 7 is a function block diagram of a multi-chamber implantable stimulation device, illustrating the basic elements of a device which can provide cardioversion, defibrillation, and pacing stimulation in four chambers of the heart, as well as direct nerve sensing.

As illustrated in FIG. 7, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and/or pacing stimulation.

A housing 40 for the stimulation device 10, shown schematically in FIG. 7, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM and/or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 7, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart 12, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram (IEGM) signals, convert the raw analog data into a digital signal, and store the digital signals for later processing and/or telemetric transmission to an external device 702, which, in certain embodiments, comprises a programmer. The data acquisition system 90 is coupled to the right atrial lead 20, the coronary sinus lead 24, and the right ventricular lead 30 through the switch 74 to sample cardiac signals across any pair of desired electrodes.

In one embodiment, the device 10 also comprises at least one connector 734 configured for connection to the leads 118 of the shielded electrode assemblies 100. Nerve signals from the leads 118 are further received by a signal processor 736. The signal processor 736 includes appropriate input impedance and buffering characteristics and, in certain embodiments, also amplifies or otherwise conditions nerve signals received from the leads 118. The output of the signal processor 736 is provided to the data acquisition system 90 which further processes the nerve signals and provides them to the microcontroller 60. In other embodiments, nerve signals are provided directly from the one or more connectors 734 to the data acquisition system 90.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, desired operating parameters or other programming instructions of the implantable device 10 may be non-invasively programmed into the memory 94 through a telemetry circuit 700 in telemetric communication with the external device 702, such as a programmer, transtelephonic transceiver, or a diagnostic system analyzer. The telemetry circuit 700 may be activated from a standby condition in response to an indication from a radio frequency (RF) detector (not shown) that signals of a predetermined strength are being received. The telemetry circuit 700 can communicate with the microcontroller 60 via a communication link 706.

The telemetry circuit 700 also advantageously allows intracardiac electrograms and status information relating to the operation of the device 10 (as contained in the microcontroller 60 or memory 94) to be sent to the external device 702 through an established communication link 104 as well as data from sensors 708. In certain embodiments, data from the sensors 708 is selectively sent continuously via the communication link 704 and, in alternative embodiments, the data from the sensors 708 is sent in frames and/or as a derived signal, e.g. an average or rate.

The device 10 comprises one or more physiologic sensor(s) 708, commonly referred to as a "rate-responsive" sensor, because it is typically used to adjust pacing stimulation rate according to the exercise state of the patient. However, the physiological sensor 708 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

While shown in FIG. 7 as being included internal to the stimulation device 10, it is to be understood that the sensors 708 may also be positioned outside and in communication with the stimulation device 10 and may include a variety of sensors 708 some or all of which may be external to the device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, ventricular gradient, etc. It is also to be understood, that in certain embodiments, the sensors 708 are capable of sensing multiple parameters and providing all the sensed parameters or a selected number of the parameters to the device 10.

In certain embodiments, the sensors 708 comprise one or more of the shielded electrode assemblies 100 as previously described such that the shielded electrode assemblies 100 in combination with the device 10 define a sensing system. In these embodiments, the shielded electrode assemblies 100 provide signals to the device 10 corresponding to sensed activity of one or more corresponding nerves 200. Thus, the device 10 can receive signals from the shielded electrodes assemblies 100 which are relatively "clean" carrying a significantly reduced level of background noise and which the device 10 can thus utilize with significantly reduced need for filtering or signal processing. The device 10 can store the signals sensed in the onboard memory 94 and/or provide the signals telemetrically to the external device 702 as previously described for further evaluation/utilization.

The device 10 can also use the sensed signals internally to evaluate the patient's condition, such as for determination of appropriate therapy delivery. In one embodiment, the shielded electrode assemblies 100 provides signals to the device 10 corresponding to sensed activity on the patient's phrenic nerve 200. In these embodiments, the device 10 is provided with signals corresponding directly to the patient's respiratory demand as indicated by phrenic nerve activity.

The device 10 can evaluate these sensed nerve activity signals with measurements of the patient's respiratory response, such as obtained by a sensor 708 configured as an impedance sensor which is arranged to measure the patient's transthoracic impedance. As the transthoracic impedance varies with the amount of air in the patient's lungs through the inhalation and expiration of the patient's breathing, the sensor 708 can determine the depth and rate of the patient's respiration in a known manner to determine a minute ventilation measure of the respiratory output of the patient. Thus, in one embodiment, the shielded electrode assemblies 100 can provide an additional indication of the patient's respiration to the device 10 to more accurately track therapeutic cardiac pacing to the patient's metabolic demand in a rate responsive manner.

The shielded electrode assemblies 100 can also provide signals to the device 10 to indicate delivery of therapy related to other physiological aspects. In one embodiment, the device 10 receives signals corresponding to phrenic nerve 200 activity that may indicate an absence or reduction in phrenic nerve 200 activity that may correspond to an episode of CSA. In these embodiments, the device 10 can then initiate an overdrive pacing therapy to treat the CSA and/or can provide direct stimulation to the phrenic nerve 200 to restore respiration. In a similar manner, the shielded electrode assemblies 100 can provide signals to the device 10 corresponding to activity of the vagus nerve 200 to induce the device 10 to provide therapeutic stimulation related to the activity of the vagus nerve 200.

The stimulation device additionally includes a battery 710 which provides operating power to all of the circuits shown in FIG. 7. For the stimulation device 10, which employs shocking therapy, the battery 710 must be capable of operating at low current drains for long periods of time, and then be capable of providing high-current pulses (for capacitor charging) when the patient requires a shock pulse. The battery 710 must also have a predictable discharge characteristic so that elective replacement time can be detected.

As further shown in FIG. 7, the device 10 is shown as having an impedance measuring circuit 712 which is enabled by the microcontroller 60 via a control signal 714. The known uses for an impedance measuring circuit 712 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 712 is advantageously coupled to the switch 74 so that any desired electrode may be used.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 716 by way of a control signal 718. The shocking circuit 716 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes and, as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Although the foregoing description has shown, described, and pointed out the fundamental novel features of the present teachings, it will be understood that various omissions, substitutions, and changes in the form of the detail of the apparatus as illustrated, as well as the uses thereof, may be made by those skilled in the art, without departing from the scope of the present teachings. Consequently, the scope of the present teachings should not be limited to the foregoing discussion, but should be defined by the appended claims.

What is claimed is:

1. A sensor for sensing the electrical activity within a nerve, the sensor comprising:
 a sensor body having a first and second surface adapted to be positioned proximate to the nerve so as to be able to sense electrical activity within the nerve;
 at least one electrode formed adjacent the first surface of the sensor body so as to be able to either sense electrical activity within the nerve or deliver electrical stimulation to the nerve when the sensor body is positioned proximate to the nerve;
 a shielding element coupled to the sensor body wherein the shielding element is insulated from the at least one electrode and wherein the shielding element comprises a plurality of openings and wherein the shielding element is adapted to shield the at least one electrode from electromagnetic radiation to improve the ability of the at least one electrode to sense electrical activity within the nerve;
 wherein the shielding element comprises a mesh of conducting material formed on the second surface;
 wherein the mesh is sized so as to inhibit electromagnetic radiation of a frequency of greater than about 10 kHz from traveling inward towards the at least one electrode; and
 wherein the mesh is formed by photolithographic deposition.

2. The sensor of claim 1, wherein the sensor body is formed of a flexible insulating material and is adapted to be positioned circumferentially about the nerve.

3. The sensor of claim 1, wherein the sensor body is generally cylindrical with the first surface being an inner surface of the generally cylindrical body and the second surface being the outer surface of the generally cylindrical body.

4. The sensor of claim 3, wherein the sensor body is contoured to have interlacing fingers which are movable between an engaged position wherein the sensor body is retained about the nerve and a disengaged position wherein an aperture extending the length of the sensor body is defined to allow for the sensor to be positioned about or removed from the nerve.

5. The sensor of claim 3, wherein the at least one electrode is formed of a metallic metal formed in the sensor body on the first surface so as to generally extend circumferentially about the outer surface of the nerve when the nerve is positioned within the inner surface of the sensor body.

6. The sensor of claim 5, wherein the at least one electrode comprises two electrodes axially spaced along the inner surface of the sensor body and formed in the sensor body on the first surface so as to generally extend circumferentially about the outer surface of the nerve when the nerve is positioned within the inner surface of the sensor body.

7. The sensor of claim 5, wherein the at least one electrode comprises a metallic foil or region of metal deposition.

8. A system for providing therapeutic stimulation to the heart of a patient, the system comprising:
 at least one lead having at least one electrode adapted to be implanted within the heart of the patient so as to sense electrical activity within the heart of the patient and to deliver electrical therapeutic stimulation to the heart of the patient;
 a nerve electrode assembly adapted to be positioned proximate a nerve so as to sense electrical activity within the nerve wherein the nerve electrode assembly includes a body that is adapted to be fixed proximate the nerve, at least one nerve electrode that senses electrical signals within the nerve and is formed proximate a first surface of the body and a shield comprising a plurality of openings that is formed proximate a second surface of the body in a location wherein the shield inhibits electromagnetic radiation from sources other than the nerve to be sensed by the at least one nerve electrode;
 a controller that receives signals from the at least one lead and the nerve electrode and uses the signals to develop therapeutic electrical stimulation to the heart of the patient via the at least one lead;
 wherein the shield comprises a mesh of conducting material formed on the second surface;
 wherein the mesh is sized so as to inhibit electromagnetic radiation of a frequency of greater than about 10 kHz from traveling inward towards the at least one nerve electrode; and
 wherein the mesh is formed by photolithographic deposition.

9. The system of claim 8, wherein the body is formed of a flexible insulating material and is adapted to be positioned circumferentially about the nerve.

10. The system of claim 8, wherein the body is generally cylindrical with the first surface being an inner surface of the generally cylindrical body and the second surface being the outer surface of the generally cylindrical body.

11. The system of claim 8, wherein the body is contoured to have interlacing fingers which are movable between an engaged position wherein the body is retained about the nerve and a disengaged position wherein an aperture extending the length of the body is defined to allow for the nerve electrode assembly to be positioned about or removed from the nerve.

12. The system of claim 8, wherein the at least one nerve electrode is formed of a metallic metal formed in the body on the first surface so as to generally extend circumferentially about the outer surface of the nerve when the nerve is positioned within the inner surface of the body.

13. The system of claim 8, wherein the at least one nerve electrode comprises two electrodes axially spaced along the inner surface of the sensor body and formed in the body on the first surface so as to generally extend circumferentially about the outer surface of the nerve when the nerve is positioned within the inner surface of the body.

14. The system of claim 8, wherein the at least one nerve electrode comprises a metallic foil or region of metal deposition.

15. The system of claim 8, wherein the controller further receives signals from the at least one lead and the nerve electrode and uses the signals to develop therapeutic electrical stimulation to the nerve of the patient via the nerve electrode.

* * * * *